United States Patent [19]
Wenstrom, Jr. et al.

[11] Patent Number: 6,019,768
[45] Date of Patent: Feb. 1, 2000

[54] SUTURE ANCHOR RETRIEVER AND METHOD FOR RETRIEVING AN IMPLANTED SUTURE ANCHOR

[75] Inventors: Richard F. Wenstrom, Jr., Norwood; William J. Reimels, Scituate, both of Mass.

[73] Assignee: Ethicon, Inc,, Somerville, N.J.

[21] Appl. No.: 08/972,860

[22] Filed: Nov. 18, 1997

[51] Int. Cl.$^7$ .................................................. A61B 17/58
[52] U.S. Cl. ............................. 606/104; 606/73; 606/232
[58] Field of Search ............................... 606/104, 73, 72, 606/232; 81/176.2, 176.3, 52, 121.1, 3.4, 3.43, 3.44, 453

[56] References Cited

U.S. PATENT DOCUMENTS

| | | | |
|---|---|---|---|
| 4,537,185 | 8/1985 | Stednitz | 128/92 B |
| 5,141,520 | 8/1992 | Goble et al. | 606/232 |
| 5,354,298 | 10/1994 | Lee et al. | 606/72 |
| 5,370,662 | 12/1994 | Stone et al. | 606/232 |
| 5,411,523 | 5/1995 | Goble | 606/232 |
| 5,607,432 | 3/1997 | Fucci | 606/104 |
| 5,667,513 | 9/1997 | Torrie et al. | 606/104 |

OTHER PUBLICATIONS

"Anchorlok™ Questus™ Leading Edge™ Soft Tissue Anchor System", 4 pages.

*Primary Examiner*—Michael Buiz
*Assistant Examiner*—Julian W. Woo
*Attorney, Agent, or Firm*—Pandiscio & Pandiscio

[57] ABSTRACT

A suture anchor retriever is adapted to remove a suture anchor from bone or other bodily member, the suture anchor being threaded and having a proximally-extending connector portion provided with a bore for receiving a suture, and having a pair of channels extending proximally to a proximal end of the connector portion. The anchor retriever comprises a stem portion having a socket portion at a distal end thereof, the socket portion being configured to fit snugly around the connector portion and within the channels so as to engage the suture anchor connector portion both externally and internally thereof, and a grip portion fixed to the stem portion at a proximal end of the stem portion. The stem portion is turnable around a lengthwise axis thereof by manipulation of the grip portion so as to bring surfaces of the socket portion to bear against complementary surfaces of the anchor connector portion, whereby to turn the anchor in the bone so as to retrieve the anchor from the bone.

20 Claims, 7 Drawing Sheets

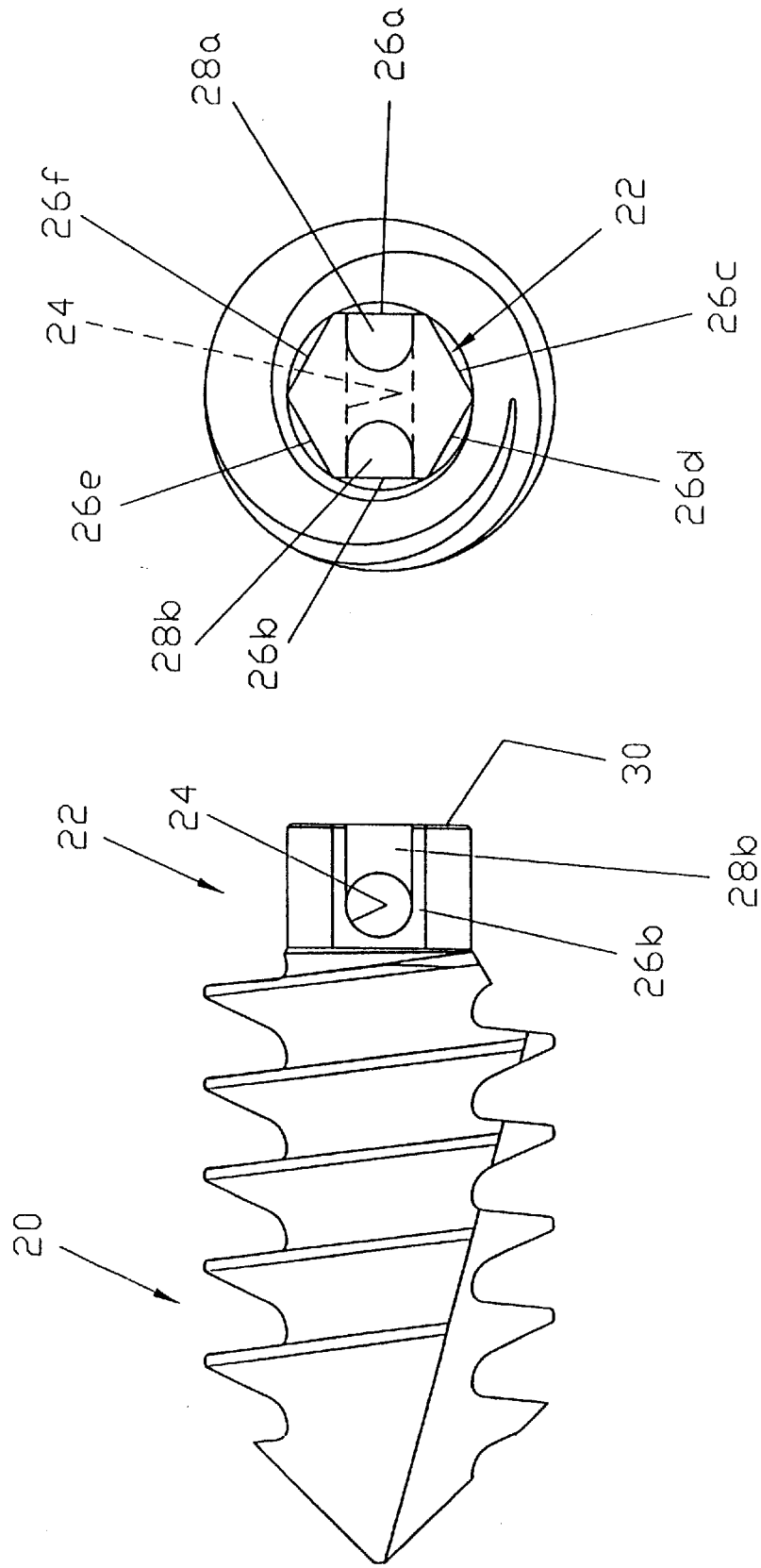

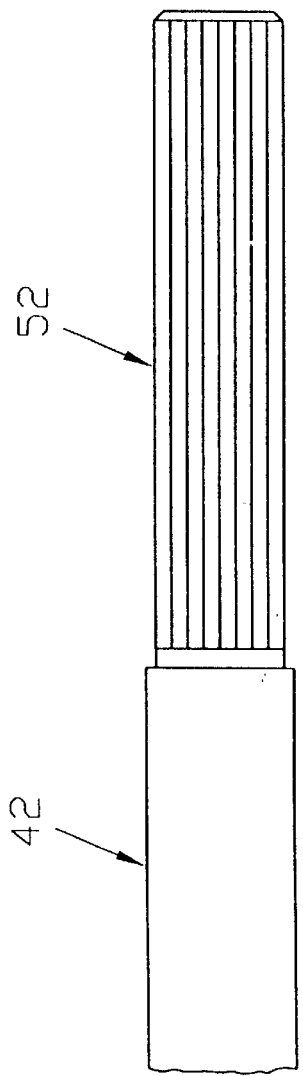
FIG. 5
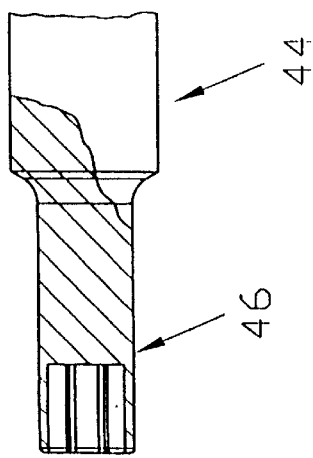
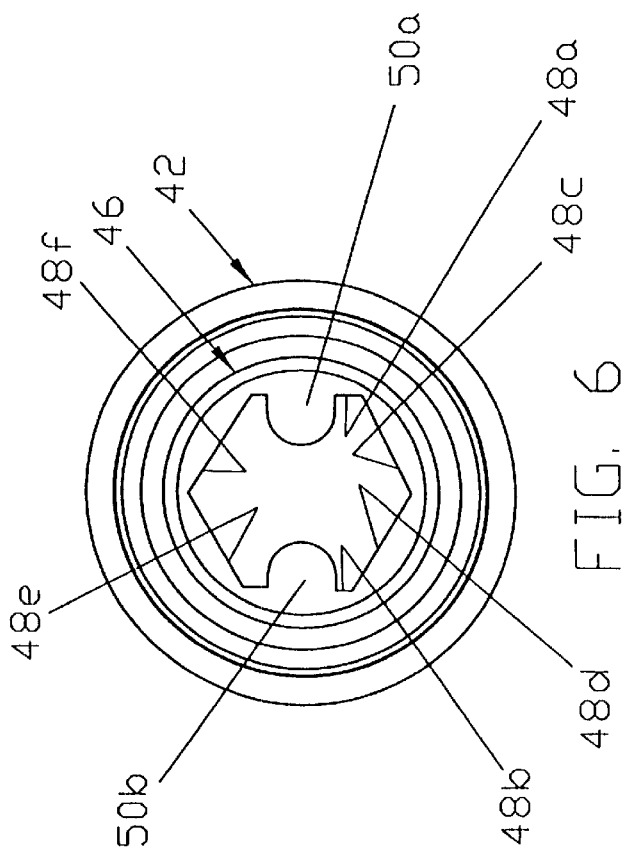
FIG. 6

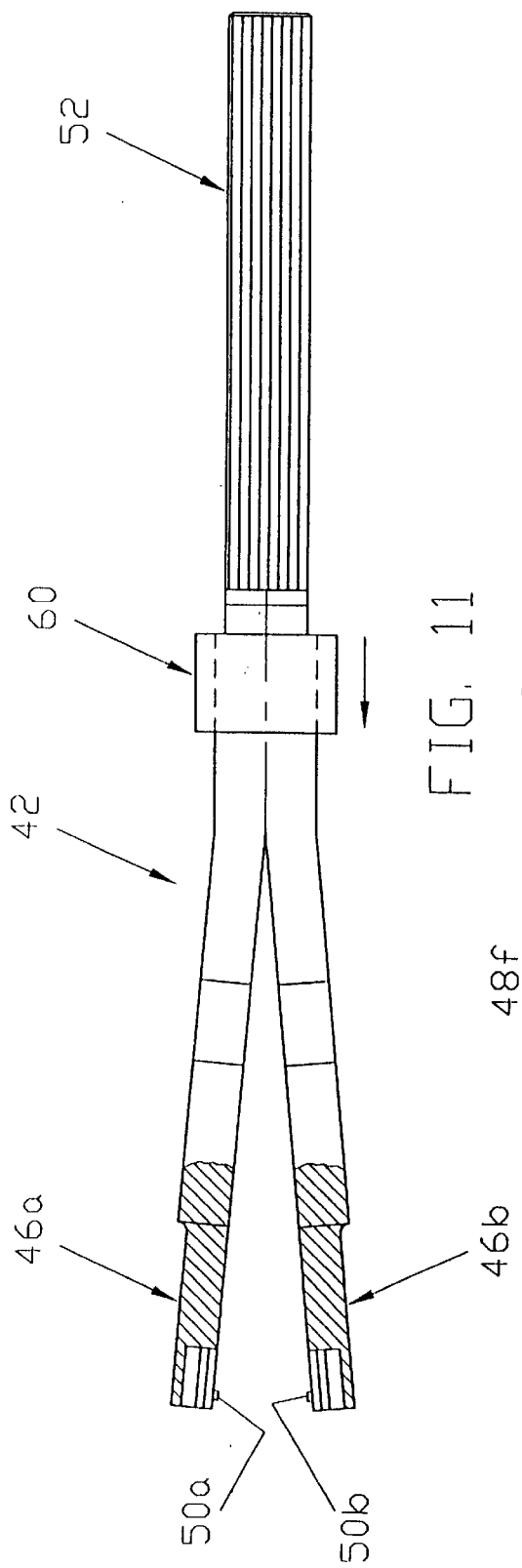
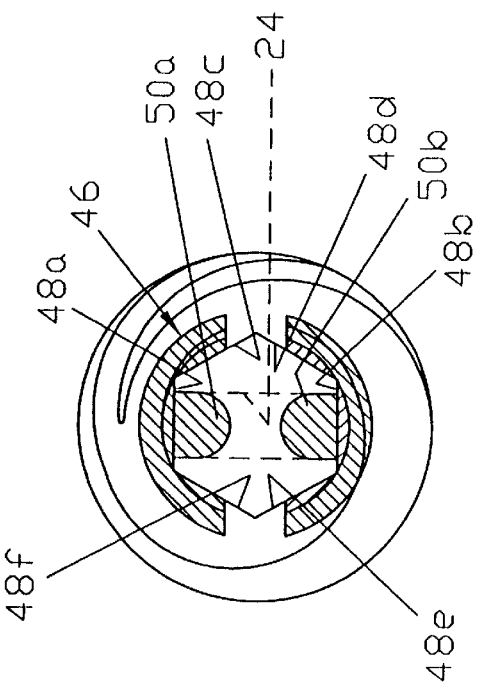
FIG. 11
FIG. 12

SUTURE ANCHOR RETRIEVER AND METHOD FOR RETRIEVING AN IMPLANTED SUTURE ANCHOR

FIELD OF THE INVENTION

This invention relates to surgical devices and procedures in general, and more particularly to a device and method for retrieving suture anchors from bone in a mammalian body.

BACKGROUND OF THE INVENTION

Suture anchors are well known in the art. Such anchors are provided with anchoring means by which the anchor is secured to a bone or other bodily part of a mammal, principally humans. The anchoring means typically comprise screw threads and/or barbs, or the like. Suture anchors further comprise means for attaching a suture to the anchor, such that once the anchor is set in a bone, the suture extends therefrom and can be used to attach a ligament, or the like, to the bone, or to support other soft tissue relative to the bone, e.g., to suspend the neck of the bladder from the pelvic bone, etc.

In U.S. patent application Ser. No. 08/393,553, filed Feb. 23, 1995 by E. Marlowe Goble et al.; U.S. Pat. No. 5,370,662, issued Dec. 6, 1994 to Kevin R. Stone et al.; and U.S. Pat. No. 5,607,432, issued Mar. 4, 1997 to Joseph Fucci, there are shown suture anchors having a threaded distal portion for anchoring the device in bone and a proximally-extending connector portion having a bore therethrough for receiving a suture.

A number of other generally similar anchor devices are well known in the art.

By and large, devices of this type have been successfully used in many surgical situations. At times, however, in the course of anchoring the device or manipulating the suture after having anchored the device, the suture breaks, usually proximate the anchor, leaving the anchor in a useless condition within the bone. Usually, the suture-less anchor is simply left in place in the bone and a new anchor, with its suture intact, is set alongside the suture-less anchor. Of course, the suture-less anchor occupies the position which was initially selected by the surgeon as the best location for the anchor, and the new anchor necessarily must be placed in a "next best" location.

It is preferable to withdraw the first anchor so that the second anchor, with its attached suture, may be put in the place of the first anchor. However, withdrawal of the first anchor from a bone requires unscrewing the anchor from the bone, which requires placing a hefty turning force on the anchor.

Accordingly, there exists a need for a suture anchor retriever and a method for unscrewing a suture anchor from bone, or other bodily part, thereby to remove the anchor from the bone or body part, such that a second anchor may be inserted in the place formerly occupied by the retrieved anchor.

OBJECTS OF THE INVENTION

Accordingly, an object of the present invention is to provide a suture anchor retriever having facility for removing a suture anchor from a bone or other bodily member.

A further object of the present invention is to provide a method for retrieving an implanted suture anchor.

SUMMARY OF THE INVENTION

The above and other objects of the present invention are addressed by the provision and use of a novel suture anchor retriever for removing a suture anchor from a bodily member, the suture anchor being threaded and having a proximally-extending connector portion provided with a bore for receiving a suture, and having a pair of channels each extending proximally from an end of the bore to a proximal end of the connector portion. The anchor retriever comprises a stem portion having a socket portion at a distal end thereof, the socket portion being configured to fit snugly around the connector portion and within the channels so as to engage the suture anchor connector portion both externally and internally thereof, and a grip portion fixed to the stem portion at a proximal end of the stem portion. The stem portion is turnable around a lengthwise axis thereof by manipulation of the grip portion so as to bring surfaces of the socket portion to bear against complementary surfaces of the anchor connector portion, whereby to turn the anchor in the bodily member so as to retrieve the anchor from the bodily member.

BRIEF DESCRIPTION OF THE DRAWINGS

These and other objects and features of the present invention will be more fully disclosed or rendered obvious by the following detailed description of the preferred embodiments of the invention, which are to be considered together with the accompanying drawings wherein like numbers refer to like parts, and further wherein:

FIG. 1 is a side elevational view of a suture anchor of the sort with which the present invention is intended to be used;

FIG. 2 is a proximal end view of the suture anchor of FIG. 1;

FIG. 5 is a partially broken away side elevational view of the stem portion of the suture anchor retriever of FIGS. 3 and 4;

FIG. 6 is a distal end view of the stem portion of FIG. 5;

FIG. 11 is similar to FIG. 5, but illustrative of an alternative embodiment of the stem portion; and FIG. 12 is similar to FIG. 6, but illustrative of the alternative embodiment of FIG. 11.

DETAILED DESCRIPTION OF THE PREFERRED EMBODIMENTS

Figure 3:
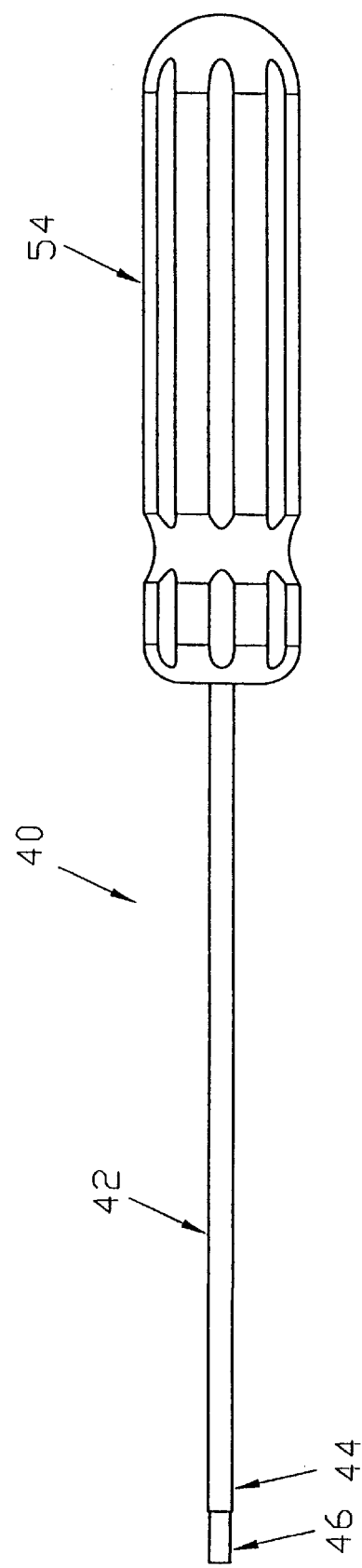
FIG. 3 is a side elevational view of a suture anchor retriever illustrative of one embodiment of the present invention.

Referring first to FIGS. 1 and 2, it will be seen that the type of suture anchor for which the novel retriever is intended to be used includes a threaded distal portion 20 and a proximally-extending connector portion 22. The connector portion 22 is provided with a widthwise extending bore 24 for receiving a suture (not shown). The connector portion 22 is typically hexagonally shaped (FIG. 2) and the bore 24 is centered on two opposed flat sides 26a, 26b of the connector portion 22. Flat sides 26c, 26d, 26e and 26f make up the remaining sides of the hexagonally shaped connector portion 22 (FIG. 2). A pair of channels 28a, 28b are formed in flat sides 26a, 26b, respectively. Channels 28a, 28b extend proximally from, and are respectively in communication with, the ends of the bore 24. The channels 28a, 28b extend to a proximal end 30 of the connector portion 22, and serve to receive a suture extending through bore 24.

By way of example but not limitation, the sort of suture anchor for which the novel retriever is intended to be used may be of the sort disclosed in U.S. patent application Ser. No. 08/393,553, filed Feb. 23, 1995 by E. Marlowe Goble et al., which application is hereby incorporated herein by reference.

The illustrative suture anchor retriever 40 (FIGS. 3 and 4) includes a stem portion 42 (FIGS. 3–5) having, at a distal end 44 thereof, a socket portion 46. The socket portion 46 is of an internal configuration complementary to the configuration of the anchor connector portion 22. In the illustrative example, where anchor connector portion 22 is hexagonally shaped, the socket portion 46 includes flat surfaces 48a, 48b, 48c, 48d, 48e, and 48f (FIG. 6), each complementary to the flat hex sides of the anchor connector portion 22. For example, socket portion surface 48a is complementary to anchor flat side 26a, socket portion surface 48b is complementary to anchor flat side 26b, and so on. Further, socket flat surfaces 48a and 48b are provided with inwardly extending detents 50a, 50b (FIG. 6) which are respectively complementary to anchor channels 28a, 28b.

Of course, if anchor connector portion 22 has a configuration other than hexagonal, socket portion 46 would have a corresponding, non-hexagonal, configuration.

Figure 4:
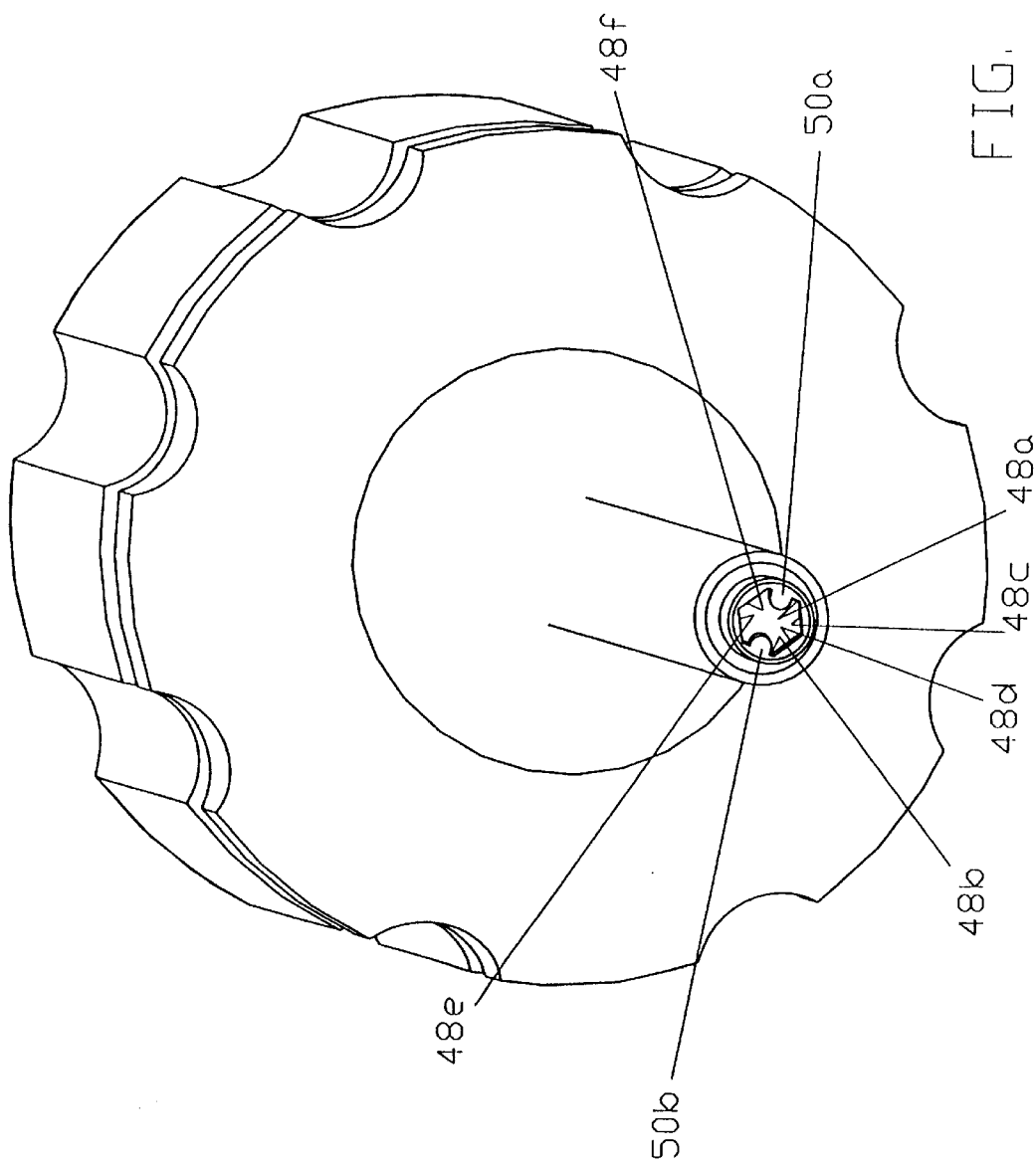
FIG. 4 is an enlarged perspective view of the suture anchor retriever of FIG. 3.
Figure 7:
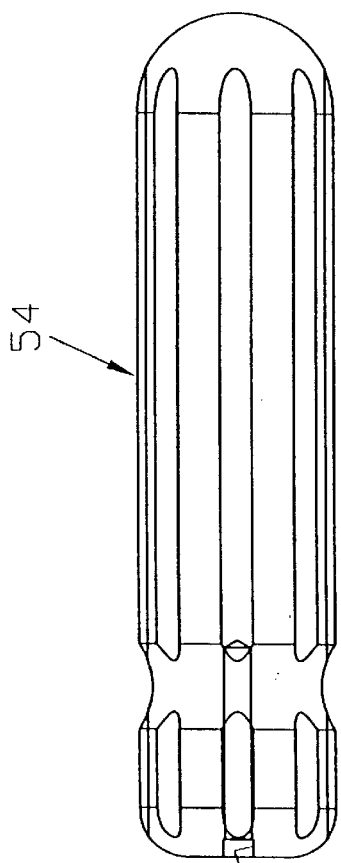
FIG. 7 is a side elevational view of the grip portion of the suture anchor retriever of FIGS. 3 and 4.
Figure 8:
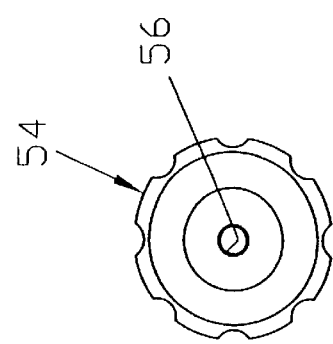
FIG. 8 is a distal end view of the grip portion of FIG. 7.
Figure 9:
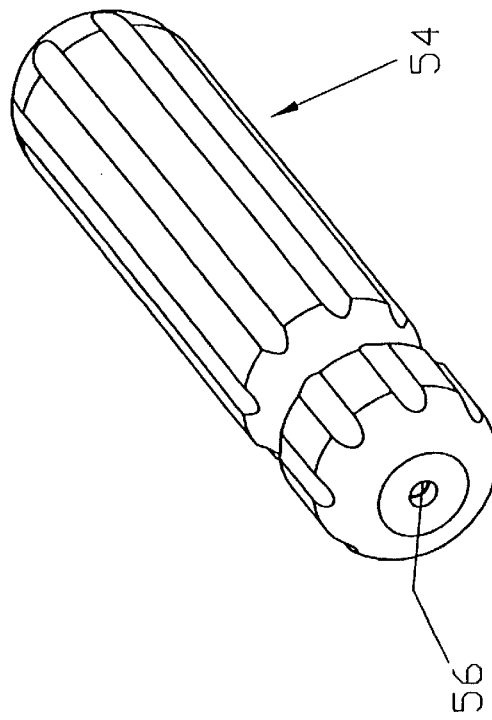
FIG. 9 is a perspective view of the grip portion of FIGS. 7 and 8.

Referring to FIG. 5, it will be seen that stem portion 42 includes a proximal portion 52 which may be rough-textured or splined so as to (1) serve as an integral grip portion, or (2) fixedly receiving a discrete grip portion. In FIGS. 3, 4 and 7–9 there is shown a discrete grip portion 54 having a central channel 56 which receives proximal portion 52 of stem portion 42 so as to complete the anchor retriever (FIGS. 3 and 4).

Figure 10:
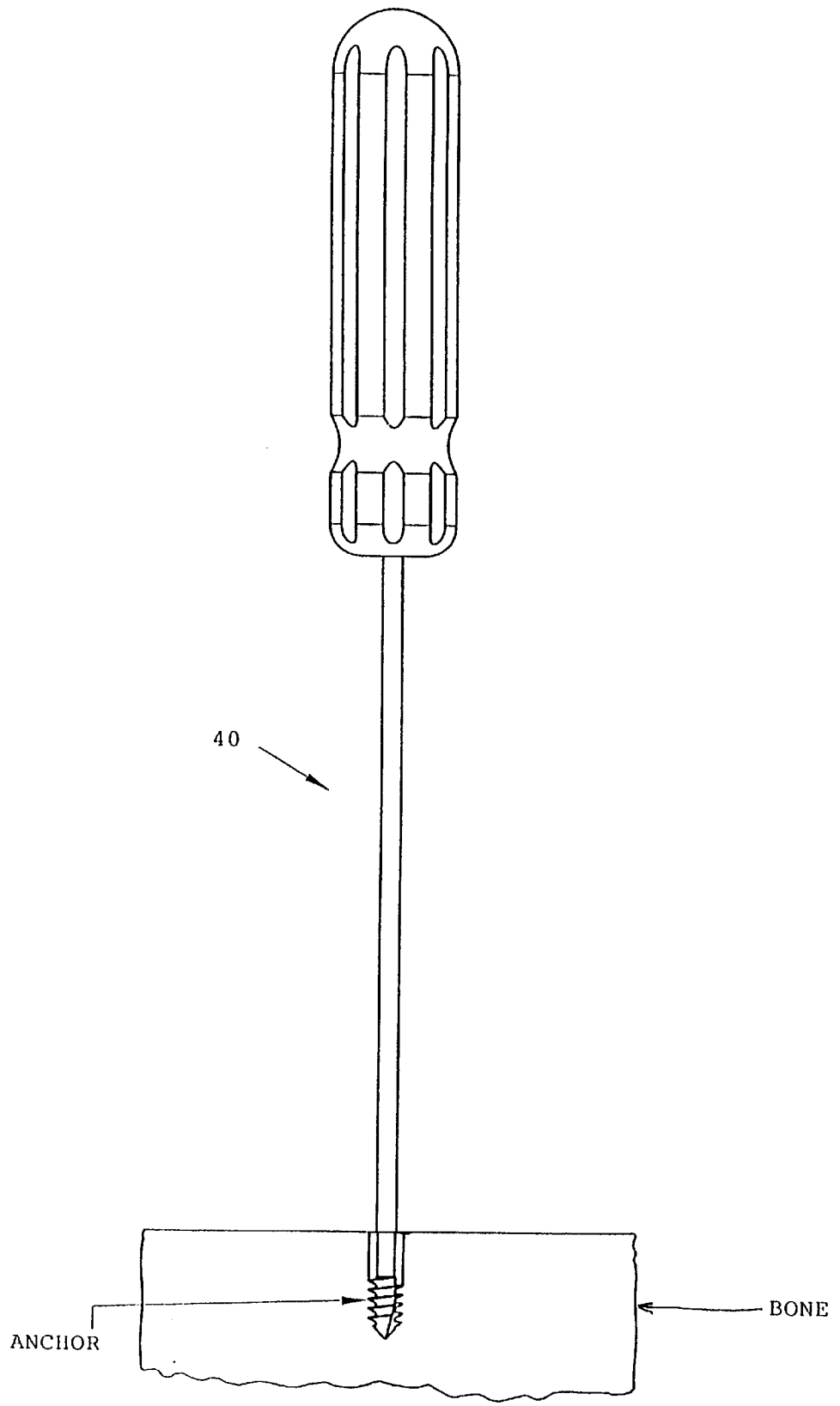
FIG. 10 is a schematic side elevational view showing the suture anchor retriever of FIGS. 3 and 4 engaging the suture anchor of FIGS. 1 and 2 while the suture anchor is disposed in bone.

In operation, when it is desired to remove a suture anchor of the type shown in FIGS. 1 and 2, the anchor retriever 40 is manipulated so as to bring the retriever's socket portion 46 onto the connector portion 22 of a suture anchor disposed in a bone (FIG. 10), such that the socket's internal flat surfaces 48a–48f engage the anchor's connector portion flat sides 28a–28f, and such that the connector portion detents 50a, 50b engage the anchor channels 28a, 28b, respectively. By manipulation of the stem proximal portion 52, or alternatively, the grip portion 54 fixed thereto, the stem portion 42 is caused to rotate counter-clockwise about its axis so as to cause counter-clockwise rotation of the suture anchor, whereby to cause the anchor to threadedly back out of the bone, or other matter, with which the anchor is engaged.

With regard to the foregoing, it is to be appreciated that anchor retriever 40 is intended to engage the implanted anchor after the suture has been removed from the anchor, e.g., either after the suture has unintentionally broken and thereby become detached from the anchor, or after the user has intentionally removed the suture from the implanted anchor, etc.

In FIGS. 11 and 12, there is illustrated an alternative embodiment in which the socket portion 46 is bifurcated into two opposed half-sockets 46a, 46b, the former having flat surfaces 48a, 48c and 48f and detent 50a, and the latter having flat surfaces 48b, 48e and 48d and detent 50b. A collar 60 (which may be a ring, as shown, or a tube or other satisfactory construction) is slidable distally over the half-sockets 46a, 46b so as to lock the half-sockets 46a, 46b securely around the anchor connector portion 22 (FIG. 12). In this embodiment, the detents 50a and 50b may extend into the anchor bore 24 (FIG. 12) further than the depth of the channels 28a, 28b for improved holding power. To facilitate movement of the detents 50a, 50b widthwise of the anchor connector portion, the stem portion 42 is bifurcated such that the half-sockets 46a, 46b may be biased in a sprung-apart condition and forced inwardly toward each other, and into the anchor bore 24, by the distal movement of the collar 60, bringing the half-sockets toward, and into, the bore 24. Thereafter, the retriever of FIGS. 11 and 12 is manipulated similarly to manipulation of the first embodiment of retriever so as to remove the anchor from its implanted site.

There is thus provided a suture anchor retriever having facility for quickly and easily removing a suture anchor from a bone or other bodily structure.

It is to be understood that the present invention is by no means limited to the particular construction herein disclosed and/or shown in the drawings, but also comprises any modifications or equivalents within the scope of the claims.

What is claimed is:

1. A suture anchor retriever for removing a suture anchor from a bodily member, the suture anchor being threaded and having a proximally-extending connector portion provided with a bore extending substantially transversely therethrough between a pair of open ends, said bore being adapted for receiving a suture, and said connector portion also defining a pair of channels, each said channel extending proximally from an open end of the bore to a proximal end of the connector portion, said anchor retriever comprising:

a stem portion having a socket portion at a distal end thereof, said socket portion having a hexagonal portion in a widthwise plane and configured to fit snugly around said anchor connector portion and within said channels so as to engage said suture anchor connector portion both externally and internally thereof; and a grip portion extending from said stem portion at a proximal end of said stem portion;

said stem portion being turnable around a lengthwise axis thereof by manipulation of said grip portion so as to bring surfaces of said socket portion to bear against complementary surfaces of the anchor connector portion, whereby to turn the anchor in the bodily member so as to retrieve the anchor from the bodily member.

2. A suture anchor retriever according to claim 1 wherein the anchor connector portion is provided with external flat sides, and said socket portion is provided internal flat surfaces complementary with and engageable with the flat sides.

3. A suture anchor retriever according to claim 2 wherein the anchor connector portion is further provided with longitudinally extending channels, and said socket portion is further provided with elongated detents complementary to the channels and adapted to be received by the channels.

4. A suture anchor retriever according to claim 1 wherein said detents extend toward one another from opposed ones of said flat surfaces.

5. A suture anchor retriever according to claim 1 wherein said grip portion comprises a proximal extension of said stem portion.

6. A suture anchor retriever according to claim 1 wherein said grip portion comprises a discrete member fixed to said proximal end of said stem portion.

7. A suture anchor retriever according to claim 1 wherein said stem portion is split axially thereof into first and second stem portions and said socket portion is split into first and second half-socket portions, said half-socket portions being movable transversely of said stem portion lengthwise axis so as to enter said channels.

8. A suture anchor retriever according to claim 7 wherein said detents include portions adapted to extend inwardly beyond the anchor channels and to enter the anchor bore.

9. A suture anchor retriever according to claim 7 and further comprising a collar mounted on said stem portion and movable distally so as to urge said half-socket portions inwardly toward each other and to retain said half-socket portions in a closed-together position.

10. A method for retrieving an implanted suture anchor having a threaded distal end portion and a proximally-extending connector portion provided with a bore extending substantially transversely therethrough between a pair of open ends, said bore being adapted for receiving a suture, and said connector portion also defining a pair of channels, each said channel extending proximally from an open end of the bore to a proximal end of the connector portion, the method comprising the steps of:

providing a suture anchor retriever comprising a stem portion having a socket portion at a distal end thereof, the socket portion having a hexagonal portion in a widthwise plane and configured to fit snugly around the anchor connector portion and within the channels so as to engage the suture anchor connector portion both externally and internally thereof, and a grip portion extending from said stem portion at a proximal end of the stem portion;

engaging the anchor connector portion with the anchor retriever socket portion such that flat surfaces of the socket portion engage flat sides of the anchor connector portion and such that detents extending inwardly toward each other from opposed ones of the socket portion flat surfaces enter the anchor connector portion channels, respectively; and turning the retriever grip portion, whereby to turn the anchor so as to remove the anchor from a member in which the anchor is implanted.

11. A method according to claim 10 wherein the stem portion is split axially thereof into first and second stem portions and the socket portion is split into first and second half-socket portions, and a collar is movable distally on the stem portion so as to engage the half-socket portions and urge the half-socket portions toward each other, and including the steps of:

placing the first and second half-socket portions each respectively adjacent one of the channels; and moving the collar distally so as to move the half-socket portions toward one another and the detents into the respective channels.

12. A method according to claim 11 wherein the detents are each provided with portions extending inwardly beyond the boundary otherwise of the detent, and the step of moving the half-sockets toward one another and the detents into the respective channels includes moving the detent extending portions into the respective ends of the bore.

13. A suture anchor retriever for removing a suture anchor from a bodily member, the suture anchor being threaded and having a proximally-extending connector portion provided with external flat sides defining a hexagonal configuration in a widthwise plane, a bore for receiving a suture, and having a pair of channels each extending longitudinally and proximally from an end of the bore to a proximal end of the connector portion, said anchor retriever comprising:

a stem portion having a socket portion at a distal end thereof, said socket portion including internal flat surfaces defining a hexagonally shaped opening and elongated detents complementary to, and adapted to be received by, said channels such that said socket portion is configured to fit snugly around said anchor connector portion and within said channels so as to engage said suture anchor connector portion both externally and internally thereof; and a grip portion extending from said stem portion at a proximal end of said stem portion;

said stem portion being turnable around a lengthwise axis thereof by manipulation of said grip portion so as to bring surfaces of said socket portion to bear against complementary surfaces of the anchor connector portion, whereby to turn the anchor in the bodily member so as to retrieve the anchor from the bodily member.

14. A suture anchor retriever according to claim 13 wherein said detents extend toward one another from opposed ones of said flat surfaces.

15. A suture anchor retriever for removing a suture anchor from a bodily member, the suture anchor being threaded and having a proximally-extending connector portion provided with a bore for receiving a suture, and having a pair of channels each extending proximally from an end of the bore to a proximal end of the connector portion, said anchor retriever comprising:

a stem portion having a socket portion at a distal end thereof, said socket portion being configured to fit snugly around said anchor connector portion and within said channels so as to engage said suture anchor connector portion both externally and internally thereof; and a grip portion extending from said stem portion at a proximal end of said stem portion;

said stem portion being split axially thereof into first and second stem portions and said socket portion being split into first and second half-socket portions, said half-socket portions being movable transversely of said stem portion lengthwise axis so as to enter said channels; and said stem portion being turnable around a lengthwise axis thereof by manipulation of said grip portion so as to bring surfaces of said socket portion to bear against complementary surfaces of the anchor connector portion, whereby to turn the anchor in the bodily member so as to retrieve the anchor from the bodily member.

16. A suture anchor retriever according to claim 15 wherein said detents include portions adapted to extend inwardly beyond the anchor channels and to enter the anchor bore.

17. A suture anchor retriever according to claim 15 and further comprising a collar mounted on said stem portion and movable distally so as to urge said half-socket portions inwardly toward each other and to retain said half-socket portions in a closed-together position.

18. A method for retrieving an implanted suture anchor having a threaded distal end portion and a proximally-extending connector portion having flat sides arranged in a hexagonal configuration in a widthwise plane, said connector portion being provided with a bore for receiving a suture, and having a pair of channels each extending proximally from an end of the bore to a proximal end of the connector portion, the method comprising the steps of:

providing a suture anchor retriever comprising a stem portion having a socket portion at a distal end thereof, the socket portion having flat surfaces defining a hexagonally-shaped opening configured to fit snugly around the anchor connector portion and within the channels so as to engage the suture anchor connector portion both externally and internally thereof, and a grip portion extending from said stem portion at a proximal end of the stem portion;

engaging the anchor connector portion with the anchor retriever socket portion such that flat surfaces of the socket portion engage flat sides of the anchor connector portion and such that detents extending inwardly toward each other from opposed ones of the socket portion flat surfaces enter the anchor connector portion channels, respectively; and turning the retriever grip portion, whereby to turn the anchor so as to remove the anchor from a member in which the anchor is implanted.

19. A method according to claim 18 wherein the stem portion is split axially thereof into first and second stem portions and the socket portion is split into first and second half-socket portions, and a collar is movable distally on the stem portion so as to engage the half-socket portions and urge the half-socket portions toward each other, and including the steps of:

placing the first and second half-socket portions each respectively adjacent one of the channels; and moving the collar distally so as to move the half-socket portions toward one another and the detents into the respective channels.

20. A method according to claim 19 wherein the detents are each provided with portions extending inwardly beyond the boundary otherwise of the detent, and the step of moving the half-sockets toward one another and the detents into the respective channels includes moving the detent extending portions into the respective ends of the bore.

* * * * *